United States Patent [19]

Hayakawa et al.

[11] Patent Number: 5,641,805
[45] Date of Patent: Jun. 24, 1997

[54] TOPICAL OPHTHALMIC FORMULATIONS FOR TREATING ALLERGIC EYE DISEASES

[75] Inventors: Eiji Hayakawa, Susono; Masashi Nakakura, Shizuoka-ken, both of Japan; Stella M. Robertson, Arlington; John Michael Yanni, Burleson, both of Tex.

[73] Assignees: Alcon Laboratories, Inc., Fort Worth, Tex.; Kyowa Hakko Kogyo Co. Ltd., Tokyo, Japan

[21] Appl. No.: 469,729

[22] Filed: Jun. 6, 1995

[51] Int. Cl.$^6$ .................................. A61K 31/335
[52] U.S. Cl. ............................................. 514/450
[58] Field of Search ............................... 514/450

[56] References Cited

U.S. PATENT DOCUMENTS

| | | | |
|---|---|---|---|
| 4,871,865 | 10/1989 | Lever, Jr. et al. | 549/354 |
| 4,923,892 | 5/1990 | Lever, Jr. et al. | 514/450 |
| 5,116,863 | 5/1992 | Oshima et al. | 514/450 |

FOREIGN PATENT DOCUMENTS

| | | |
|---|---|---|
| 0048023A2 | 3/1982 | European Pat. Off. |
| 0214779A1 | 3/1987 | European Pat. Off. |
| 0235796A2 | 9/1987 | European Pat. Off. |

OTHER PUBLICATIONS

Kamei et al., "Effects of Certain Antiallergic Drugs on Experimental Conjunctivitis in Guinea Pigs," *Atarashi Ganka*, vol. 11(4), pp. 603–605 (1994) (abstract only).

Kamei et al., "Effect of (Z)–11–[3–(Dimethylamino) propylidene]–6,11–dihydrodibenz[b,e]oxepin–2–acetic Acid Hydrochloride on Experimental Allergic Conjunctivitis and Rhinitis in Rats and Guinea Pigs," *Arzneimittelforschung*, vol. 45(9), pp. 1005–1008 (1985).

Ohsima et al., "Synthesis and Antiallergic Activity of 11–(Aminoalkylidene)–6,11,dihydrodibenz[b,e]oxepin Derivatives," *J. Medicinal Chemistry*, vol. 35(11), pp. 2074–1084 (1992).

Sharif et al., "Characterization of the Ocular Antiallergic and Antihistaminic Effects of Olopatadine (AL–4943A), a Novel Drug for Treating Ocular Allergic Diseases," *J. of Pharmacology and Experimental Therapeutics*, vol. 278(3), pp. 1252–1261 (1996).

Sharif et al., "Olopatadine (AL–4943A): Pharmacological Profile of a Novel Anti–histaminic/Anti–allergic Drug for Use in Allergic Conjunctivitis," *Investigative Ophthalmology & Visual Science*, vol. 37(3), p. 1027 (1996) (abstract only).

Spitalny et al., "Olopatadine Ophthalmic Solution Decreases Itching and Redness Associated with Allergic Conjunctivitis," *Investigative Ophthalmology & Visual Science*, vol. 37(3), p. 593 (1996) (abstract only).

Yanni et al., "The In Vitro and In Vivo Ocular Pharmacology of Olopatadine (AL–4943A), An Effective Anti–allergic/ AntihistamIinic Agent," *Investigative Ophthalmology & Visual Science*, vol. 37(3), p. 1028 (1996) (abstract only).

Zhang et al., "Optically Active Analogues of Ebastine: Synthesis and Effect of Chirality on Their Antihistaminic and Antimuscarinic Activity," *Chirality*, vol. 6(8), pp. 631–641 (1994).

Church, "Is Inhibition of Mast Cell Mediator Release Relevant to the Clinical Activity of Anti–allergic Drugs?," *Agents and Actions*, vol. 18, 3/4, pp. 288–293 (1986).

Clegg et al., "Histamine Secretion from Human Skin Slices Induced by Anti–IgE and Artificial Secretagogues and the Effects of Sodium Cromoglycate and Salbutanol," *Clin Allergy*, vol. 15, pp. 321–328 (1985).

Hamilton et al., "Comparison of a New Antihistaminic and Antiallergic Compound KW 4679 with Terfenadine and Placebo on Skin and Nasal Provocation in Atopic Individuals," *Clinical and Experimental Allergy*, vol. 24, pp. 955–959 (1994).

Ikeda et al., "Effects of Oxatomide and KW–4679 on Acetylcholine–Induced Responses in the Isolated Acini of Guinea Pig Nasal Glands," *Int. Arch. Allergy Immunol.*, vol. 106, pp. 157–162 (1995).

Irani et al., "Mast Cell Heterogeneity," *Clinical and Experimental Allergy*, vol. 19, pp. 143–155 (1989).

Pearce et al., "Effect Disodium Cromoglycate on Antigen Evoked Histamine Release in Human Skin," *Clinical Exp. Immunol.*, vol. 17, pp. 437–440 (1974).

Siraganian, "An Automated Continuous Flow System for the Extraction and Fluorometric Analysis of Histamine," *Anal. Biochem.*, vol. 57, pp. 383–394 (1974).

"The Lung," *Scientific Foundations*, Raven Press, Ltd., New York, Ch. 3.4.11 (1991), Schwartz, pp. 601–615.

Kamei et al. "Effect of Certain Antirallergic Drugs on Experimental Conjunctivitis in Guinea Pigs", Atarashii Ganka 11(4) pp. 603–605 1994 (month unavailable).

*Primary Examiner*—Jeffrey C. Mullis
*Attorney, Agent, or Firm*—Patrick M. Ryan

[57] ABSTRACT

Topical ophthalmic formulations of the invention contain as an active ingredient 11-(3-dimethylaminopropylidene)-6,11-dihydrodibenz[b,e]oxepin-2-acetic acid or a pharmaceutically acceptable salt thereof. The formulations are useful for treating allergic eye diseases such as allergic conjunctivitis, vernal conjunctivitis, vernal keratoconjunctivitis, and giant papillary conjunctivitis.

12 Claims, No Drawings

TOPICAL OPHTHALMIC FORMULATIONS FOR TREATING ALLERGIC EYE DISEASES

BACKGROUND OF THE INVENTION

1. Field of the Invention

The present invention relates to topical ophthalmic formulations used for treating allergic eye diseases, such as allergic conjunctivitis, vernal conjunctivitis, vernal keratoconjunctivitis, and giant papillary conjunctivitis. More particularly, the present invention relates to therapeutic and prophylactic topical use of 11-(3-dimethylaminopropylidene)-6,11-dihydrodibenz[b,e]oxepin-2-acetic acid for treating and/or preventing allergic eye diseases.

2. Description of the Related Art

As taught in U.S. Pat. Nos. 4,871,865 and 4,923,892, both assigned to Burroughs Wellcome Co. ("the Burroughs Wellcome Patents"), certain carboxylic acid derivatives of doxepin, including 11-(3-dimethylaminopropylidene)-6,11-dihydrodibenz[b,e]oxepine-2-carboxylic acid and 11-(3-dimethylaminopropylidene)-6,11-dihydrodibenz[b,e]oxepine-2(E)-acrylic acid, have antihistamine and antiasthmatic activity. These two patents classify the carboxylic acid derivatives of doxepin as mast cell stabilizers with antihistaminic action because they are believed to inhibit the release of autacoids (i.e., histamine, serotonin, and the like) from mast cells and to inhibit directly histamine's effects on target tissues. The Burroughs Wellcome Patents teach various pharmaceutical formulations containing the carboxylic acid derivatives of doxepin; Example 8 (I) in both of the patents discloses an ophthalmic solution formulation.

Although both of the Burroughs Wellcome Patents claim that the variety of pharmaceutical formulations disclosed are effective both for veterinary and for human medical use, neither patent contains an example demonstrating that the carboxylic acid derivatives of doxepin have activity in humans. Example 7 in the Burroughs Wellcome Patents demonstrates antihistamine activity in male guinea pigs and Example G demonstrates anaphylactoid activity in Wistar rats.

It is now well established, however, that the types of mast cells which exist in rodents are different from those in humans. See, for example, THE LUNG: Scientific Foundations, Raven Press, Ltd., New York, Ch. 3.4.11 (1991). Moreover, mast cell populations exist within the same species that differ in phenotype, biochemical properties, functional and pharmacological responses and ontogeny. These recognized differences in mast cells both between and within species are referred to as mast cell heterogeneity. See for example, Irani et al., "Mast Cell Heterogeneity," Clinical and Experimental Allergy, Vol. 19, pp. 143–155 (1989). Because different mast cells exhibit different responses to pharmacological agents, it is not obvious that compounds claimed to be anti-allergic ("mast cell stabilizers") will have clinical utility in specific mast cell populations. The assumption that mast cells are a homogeneous population and that therefore the effects of anti-allergic drugs observed in experiments in rat mast cells would be predictive of those in human cells is known to be incorrect. Church, "Is Inhibition of Mast Cell Mediator Release Relevant to the Clinical Activity of Anti-Allergic Drugs?," Agents and Actions, Vol. 18, 3/4, 288–293, at 291 (1986).

Examples exist in the art in which mast cell stabilizing drugs inhibit only select populations of mast cells. Disodium cromoglycate is an anti-allergic drug whose local effects are believed to be due to inhibition of mast cell degranulation (Church, Agents and Actions, at 288). This drug was shown to inhibit rodent mast cell degranulation. In human trials, 100 µM of the drug inhibited mast cells obtained from bronchoalveolar lavage fluid. In dispersed human lung mast cell preparations, 1000 µM of the drug was required to inhibit only 25% to 33% of histamine release. Finally, histamine release from human skin mast cells was not inhibited at all by disodium cromoglycate. Pearce et al., "Effect of Disodium Cromoglycate on Antigen Evoked Histamine Release in Human Skin," Clinical Exp. Immunol., Vol. 17, 437–440 (1974); and Clegg et al., "Histamine Secretion from Human Skin Slices Induced by Anti-IgE and Artificial Secretagogues and the Effects of Sodium Cromoglycate and Salbutanol," Clin. Allergy, Vol. 15, 321–328 (1985). These data clearly indicate that classification of a drug as an anti-allergic does not predict that the drug possess inhibitory effects on all mast cell populations.

Topical ophthalmic formulations which contain drugs having conjunctival mast cell activity may only need to be applied once every 12–24 hours instead of once every 2–4 hours. One disadvantage to the ophthalmic use of reported anti-allergic drugs which in fact have no human conjunctival mast cell stabilizing activity is an increased dosage frequency. Because the effectiveness of ophthalmic formulations containing drugs which do not have conjunctival mast cell activity stems primarily from a placebo effect, more frequent doses are typically required than for drugs which do exhibit conjunctival mast cell activity.

U.S. Pat. No. 5,116,863, assigned to Kyowa Hakko Kogyo Co., Ltd., ("the Kyowa patent"), teaches that acetic acid derivatives of doxepin and, in particular, the cis form of the compound having the formula

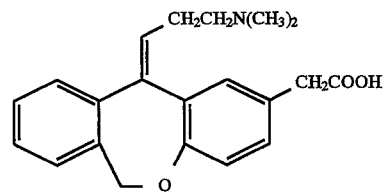

(i.e., Z-11-(3-dimethylaminopropylidene)-6,11-dihydrodibenz[b,e]oxepin-2-acetic acid), have anti-allergic and anti-inflammatory activity.

The Kyowa patent demonstrates anti-allergic activity and anti-inflammatory activity in Wistar male rats. Medicament forms taught by the Kyowa patent for the acetic acid derivatives of doxepin include a wide range of acceptable carriers; however, only oral and injection administration forms are mentioned. In the treatment of allergic eye disease, such as allergic conjunctivitis, such administration methods require large doses of medicine.

What is needed are topically administrable drug compounds which have demonstrated stabilizing activity on mast cells obtained from human conjunctiva, the target cells for treating allergic eye diseases. What is also needed are local administration methods for the treatment of allergic eye disease.

SUMMARY OF THE INVENTION

The present invention provides a method for treating an allergic eye disease characterized by administering to the eye a topical ophthalmic formulation which contains a therapeutically effective amount of 11-(3- dimethylaminopropylidene) -6,11-dihydrodibenz[b,e]oxepin-2-acetic acid (referred to as "Compound A" hereinafter) or a pharmaceutically acceptable salt thereof. The formulation may contain the cis isomer of Compound A (Z-11-(3-dimethylaminopropylidene)-6,11-dihydrodibenz[b,e]oxepin-2-acetic acid), the trans isomer of Compound A (E-11-(3-dimethylaminopropylidene)-6,11-dihydrodibenz[b,e]oxepin-2-acetic acid), or a combination of both the cis and the trans isomers of Compound A, and unless specified otherwise,"11-(3-dimethylaminopropylidene)-6,11-dihydrodibenz[b,e]oxepin-2-acetic acid" or "Compound A" means the cis isomer, the trans isomer or a mixture of both. "Cis isomer" means the cis isomer substantially free of the trans isomer; "trans isomer" means the trans isomer substantially free of the cis isomer. One isomer is "substantially free" of the other isomer if less than about two percent of the unwanted isomer is present.

Compound A has human conjunctival mast cell stabilizing activity, and may be applied as infrequently as once or twice a day in some cases. In addition to its mast cell stabilizing activity, Compound A also possesses significant antihistaminic activity. Thus, in addition to a prophylactic effect, Compound A will also have a therapeutic effect.

DETAILED DESCRIPTION OF THE INVENTION

Compound A is a known compound and both the cis and the trans isomers of Compound A can be obtained by the methods disclosed in U.S. Pat. No. 5,116,863, the entire contents of which are hereby incorporated by reference in the present specification.

Examples of the pharmaceutically acceptable salts of Compound A include inorganic acid salts such as hydrochloride, hydrobromide, sulfate and phosphate; organic acid salts such as acetate, maleate, fumarate, tartrate and citrate; alkali metal salts such as sodium salt and potassium salt; alkaline earth metal salts such as magnesium salt and calcium salt; metal salts such as aluminum salt and zinc salt; and organic amine addition salts such as triethylamine addition salt (also known as tromethamine), morpholine addition salt and piperidine addition salt.

The inhibitory effects of reported anti-allergic, mast cell stabilizing drugs on mast cells obtained from human conjunctiva (the target cells for topical ophthalmic drug preparations claimed useful in treating allergic conjunctivitis) were tested according to the following experimental method. Human conjunctival tissues obtained from organ/tissue donors were weighed and transferred to petri dishes containing RPMI 1640 culture medium supplemented with heat inactivated fetal bovine serum (20%, v/v), L-glutamine (2 mM), penicillin (100 units/ml), streptomycin (100 µg/ml), amphotericin B (2.5 µg/ml) and HEPES (10 mM) and equilibrated overnight at 37° C. (5% $CO_2$).

Post equilibration, tissues were placed in Tyrode's buffer (in mM: 137 NaCl, 2.7 KCl, 0.35 Na $H_2PO_4$, 1.8 $CaCl_2$, 0.98 $MgCl_2$, 11.9 Na $HCO_3$, 5.5 glucose) containing 0.1% gelatin (TGCM) and incubated with 200 U each of collagenase (Type IV) and hyaluronidase (Type I-S) per gram of tissue for 30 minutes at 37° C. Following enzyme digestion, tissues were washed with an equal volume of TGCM over Nitex® filter cloth (Tetko, Briarcliff Manor, N.Y.). Intact tissues were placed in TGCM for further enzymatic digestions.

The flitrate obtained from each digestion was centrifuged (825 g, 7 minutes) and pelleted cells were resuspended in calcium/magnesium free Tyrode's buffer (TG). Pooled cells from all digestions were centrifuged (825 g, 30 minutes) over a 1.058 g/L Percoll® cushion. Mast cell enriched cell pellets were resuspended and washed in TG buffer. Viability and number of mast cells were determined by vital dye exclusion and toluidine blue 0 staining of the harvested cell suspensions. Mast cell containing preparations were placed in supplemented RPMI 1640 culture medium and allowed to equilibrate at 37° C. prior to challenge with anti-human IgE (goat derived IgG antibody).

Cell suspensions containing 5000 mast cells were added to TGCM containing tubes and challenged with anti-human IgE. The final volume of each reaction tube was 1.0 mL. Tubes were incubated at 37° C. for 15 minutes post challenge. The release reaction was terminated by centrifugation (500 g, 7 minutes). Supernatants were collected and stored (−20° C.) until mediator analyses.

Initially, supernatants were analyzed for histamine content by both the automated fluorimetric method described by Siraganian, "An Automated Continuous Flow System for the Extraction and Fluorometric Analysis of Histamine," *Anal. Biochem.*, Vol. 57, 383–94 (1974), and a commercially available radioimmunoassay (RIA) system (AMAC, Inc., Westbrook, Me.). Results from these assays were positively correlated (r=0.999): therefore, the remainder of histamine analyses were performed by RIA.

Each experiment included an anti-human IgE (plus vehicle) positive release control, a spontaneous/vehicle release and a total histamine release control. Total histamine release was determined by treatment with Triton X-100® (0.1%). The experiments also included a non-specific goat IgG control. Test compounds are administered to the mast cell cultures either 1 or 15 minutes before stimulation with anti-human IgE. Inhibition of histamine release resulting from challenge of drug treated mast cells was determined by direct comparison with histamine release from vehicle treated, anti-IgE challenged mast cells using Dunnett's t-test (Dunnett, "A multiple comparison procedure for comparing treatments with a control, " *J. Amer. Stat Assoc.*, Vol. 50, 1096–1121 (1955)). The results are reported in Table 1, below.

As Table 1 clearly shows, the anti-allergic drugs disodium cromoglycate and nedocromil failed to significantly inhibit human conjunctival mast cell degranulation. In contrast, Compound A (cis isomer) produced concentration-dependent inhibition of mast cell degranulation.

TABLE 1

Compound Effect on Histamine Release from Human Conjunctival Tissue Mast Cells upon anti-Human IgE Challenge.

| Compound | Dose (µM) | Treatment (min) | Inhibition (%) |
| --- | --- | --- | --- |
| Cromolyn sodium | 1000 | 15 | −15.4 |
|  | 300 | 15 | −6.9 |
|  | 100 | 15 | −1.2 |
|  | 30 | 15 | 1.8 |
|  | 10 | 15 | 10.6 |
| Cromolyn sodium | 1000 | 1 | −9.4 |
|  | 300 | 1 | −1.8 |
|  | 100 | 1 | 1.2 |
|  | 30 | 1 | 0.1 |
|  | 10 | 1 | −0.9 |
| Nedocromil sodium | 1000 | 15 | 7.2 |
|  | 300 | 15 | 11.3 |
|  | 100 | 15 | 28.2* |
|  | 30 | 15 | 15.2 |
|  | 10 | 15 | 9.2 |
|  | 3 | 15 | 13.2 |
|  | 1 | 15 | 10.7 |

TABLE 1-continued

Compound Effect on Histamine Release from Human Conjunctival Tissue Mast Cells upon anti-Human IgE Challenge.

| Compound | Dose (µM) | Treatment (min) | Inhibition (%) |
|---|---|---|---|
| | 0.3 | 15 | 3.7 |
| | 0.1 | 15 | 8.7 |
| Nedocromil sodium | 1000 | 1 | −1.1 |
| | 300 | 1 | 4.0 |
| | 100 | 1 | 6.7 |
| | 30 | 1 | −0.9 |
| | 10 | 1 | −6.5 |
| | 3 | 1 | 0.8 |
| | 1 | 1 | 4.8 |
| | 0.3 | 1 | 8.8 |
| | 0.1 | 1 | 17.4 |
| Compound A | 2000 | 15 | 92.6* |
| | 1000 | 15 | 66.7* |
| | 600 | 15 | 47.5* |
| | 300 | 15 | 29.6* |
| | 100 | 15 | 13.0 |
| | 30 | 15 | −3.9 |

*$p < 0.05$, Dunnett's t-test

Dunnett's t-test, is a statistical test which compares multiple treatment groups with one control group. In the assay described above, histamine released from drug treated mast cells are compared to histamine released from the anti-human IgE plus vehicle treated mast cells which serve as the positive control. Statistically significant inhibition is determined using this procedure. The probability level of 0.05 is accepted as the level of significance in biomedical research. Data indicated as significant have a low probability (0.05) of occurring by chance, indicating that the inhibition observed is an effect of the drug treatment.

The effects of the cis and trans isomers of Compound A on histamine release from human conjunctival tissue mast cells upon anti-human IgE challenge are compared in Table 2. The same experimental method used in Table 1 was used in Table 2. The results in Table 2 indicate that there is no statistically significant difference between the conjunctival mast cell activity of the two isomers at the indicated dose level.

TABLE 2

Isomeric Effect of Compound A on In-Vitro Histamine Release from Human Conjunctival Tissue Mast Cells upon anti-Human IgE Challenge.

| Compound | Dose (µM) | Treatment (min) | Inhibition (%) |
|---|---|---|---|
| Compound A (cis) | 500 | 15 | 29.7*∓ |
| Compound A (trans) | 500 | 15 | 26.2*∓ |

*$p < 0.05$, Dunnett's t-test compared to anti-IgE positive control.
∓not significantly different; $p > 0.05$ Studentized Range comparison of indicated doses The topical activity of Compound A was tested in a passive anaphylaxis assay performed in rat conjunctiva. This assay indicates whether a topically applied compound effectively prevents or decreases the local allergic response in the conjunctiva. This assay allows an assessment of bioavailability following topical dosing. Briefly, male Sprague Dawley rats (6/group) were passively sensitized by subconjunctival injection of a rat serum containing IgE specific for ovalbumin (OA). Twenty-four hours post sensitization, test compound prepared in saline (0.9% NaCl) or saline vehicle was applied topically onto the sensitized eye. Twenty (20) minutes after dosing, rats were challenged intravenously via the lateral tail vein with 1.0 ml of a solution containing OA (1.0 mg/ml) and Evans Blue dye (2.5 mg/ml). Thirty (30) minutes post antigen challenge, animals were killed, skin was reflected, and the size of the resulting wheal and the intensity of the extravasated dye were determined. The wheal area multiplied by the dye intensity produced the individual response score. Scores for each group of animals were compared with the scores of the saline treated group using Dunnett's test and are listed in Table 3.

TABLE 3

In-Vivo Effects of Compound A on Passive Conjunctival Anaphylaxis in Rats

| Compound | Conc. (%, w/v) | Permeability Score ($\bar{x} \pm$ S.D.) | % Change |
|---|---|---|---|
| NaCl | 0.9 | 239 ± 22 | — |
| Compound B | 0.1 | 133 ± 53* | −55 |
| Compound C | 0.1 | 139 ± 36* | −53 |
| Compound A (cis) | 0.1 | 55 ± 56*@ | −86 |
| Compound A (trans) | 0.1 | 43 ± 34*@ | −81 |

*$p < 0.01$, Dunnett's test
@$p < 0.05$, Studentized Range Comparison Procedure, significantly different from Compounds B and C.
Compound B = (Z)-11-(3-Dimethylaminopropylidene)-6,11-dihydrodibenz[b,e]oxepin-2-carboxylic acid
Compound C = (Z)-11-(3-Dimethylaminopropylidene)-6,11-dihydrodibenz[b,e]oxepin-2-acrylic acid Compound A may be administered to the eye by means of conventional topical ophthalmic formulations, such as solutions, suspensions or gels. The preferred formulation for topical ophthalmic administration of Compound A is a solution. The solution is administered as eye drops. The preferred form of Compound A in the topical ophthalmic formulations of the present invention is the cis isomer. A general method of preparing the eye drops of the present invention is described below.

Compound A and an isotonic agent are added to sterilized purified water, and if required, a preservative, a buffering agent, a stabilizer, a viscous vehicle and the like are added to the solution and dissolved therein. The concentration of Compound A is 0.0001 to 5 w/v %, preferably 0.001 to 0.2 w/v %, and most preferably about 0.1 w/v %, based on the sterilized purified water. After dissolution, the pH is adjusted with a pH controller to be within a range which allows the use as an ophthalmologic medicine, preferably within the range of 4.5 to 8.

Sodium chloride, glycerin or the like may be used as the isotonic agent; p-hydroxybenzoic acid ester, benzalkonium chloride or the like as the preservative; sodium hydrogenphosphate, sodium dihydrogenphosphate, boric acid or the like as the buffering agent; sodium edetate or the like as the stabilizer; polyvinyl alcohol, polyvinyl pyrrolidone, polyacrylic acid or the like as the viscous vehicle; and sodium hydroxide, hydrochloric acid or the like as the pH controller.

If required, other ophthalmologic chemicals such as epinephrine, naphazoline hydrochloride, berberine chloride, sodium azulenesulfonate, lysozyme chloride, glycyrrhizate and the like may be added.

The eye drops produced by the above method typically need only be applied to the eyes a few times a day in an amount of one to several drops at a time, though in more severe cases the drops may be applied several times a day. A typical drop is about 30 µl.

Certain embodiments of the invention are illustrated in the following examples.

Example 1: Preferred Topical Ophthalmic Solution Formulation

| Ingredient | Concentration (W/V %) |
| --- | --- |
| Compound A.HCl | 0.111* |
| Dibasic Sodium Phosphate (Anhydrous), USP | 0.5 |
| Sodium Chloride, USP | 0.65 |
| Benzalkonium Chloride | 0.01 |
| Sodium Hydroxide, NF | q.s. pH = 7.0 |
| Hydrochloric Acid, NF | q.s. pH = 7.0 |
| Purified Water | q.s. 100 |

*0.111% Compound A.HCl is equivalent to 0.1% Compound A

Example 2: Topical Opthalmic Gel Formulation

| Ingredient | Concentration (W/V %) |
| --- | --- |
| Compound A.HCl | 0.11* |
| Carbopol 974 P | 0.8 |
| Disodium EDTA | 0.01 |
| Polysorbate 80 | 0.05 |
| Benzalkonium Chloride, Solution | 0.01 + 5 xs |
| Sodium Hydroxide | q.s. pH 7.2 |
| Hydrochloric acid | q.s. pH 7.2 |
| Water for Injection | q.s. 100 |

*0.11% Compound A.HCl is equivalent to 0.1% Compound A

What is claimed is:

1. A method for treating allergic eye diseases in humans comprising stabilizing conjuctival mast cells by topically administering to the eye a composition comprising a therapeutically effective amount of 11-(3-dimethylaminopropylidene)-6,11-dihydrodibenz(b,e)oxepin-2-acetic acid or a pharmaceutically acceptable salt thereof.

2. The method of claim 1 wherein the composition is a solution and the amount of 11-(3-dimethylaminopropylidene)-6,11-dihydrodibenz[b,e]oxepin-2-acetic acid is from about 0.0001 w/v. % to about 5% (w/v).

3. The method of claim 2 wherein the amount of 11-(3-dimethylaminopropylidene)-6,11-dihydrodibenz[b,e]oxepin-2-acetic acid is from about 0.001 to about 0.2% (w/v).

4. The method of claim 3 wherein the amount of 11-(3-dimethylaminopropylidene)-6,11-dihydrodibenz[b,e]oxepin-2-acetic acid is about 0.1% (w/v).

5. The method of claim 1 wherein the 11-(3-dimethylaminopropylidene)-6,11-dihydrodibenz[b,e]oxepin-2-acetic acid is (Z)-11-(3-dimethylaminopropylidene)-6,11-dihydrodibenz[b,e]oxepin-2-acetic acid, substantially free of (E)-11-(3-dimethylaminopropylidene)-6,11-dihydrodibenz[b,e]oxepin-2-acetic acid.

6. The method of claim 5 wherein the amount of (Z)-11-(3-dimethylaminopropylidene)-6,11-dihydrodibenz[b,e]oxepin-2-acetic acid is from about 0.0001 to about 5% (w/v).

7. The method of claim 6 wherein the amount of (Z)-11-(3-dimethylaminopropylidene)-6,11-dihydrodibenz[b,e]oxepin-2-acetic acid is from about 0.001 to about 0.2% (w/v).

8. The method of claim 7 wherein the amount of (Z)-11-(3-dimethylaminopropylidene)-6,11-dihydrodibenz[b,e]oxepin-2-acetic acid is 0.1% (w/v).

9. The method of claim 1 wherein the 11-(3-dimethylaminopropylidene)-6,11-dihydrodibenz[b,e]oxepin-2-acetic acid is (E)-11-(3-dimethylaminopropylidene)-6,11-dihydrodibenz[b,e]oxepin-2-acetic acid, substantially free of (Z)-11-(3-dimethylaminopropylidene)-6,11-dihydrodibenz[b,e]oxepin-2-acetic acid.

10. The method of claim 9 wherein the amount of (E)-11-(3-dimethylaminopropylidene)-6,11-dihydrodibenz[b,e]oxepin-2-acetic acid is from about 0.0001 to about 5% (w/v).

11. The method of claim 10 wherein the amount of (E)-11-(3-dimethylaminopropylidene)-6,11-dihydredibenz[b,e]oxepin-2-acetic acid is from about 0.001 to about 0.2% (w/v).

12. The method of claim 11 wherein the amount of (E)-11-(3-dimethylaminopropylidene)-6,11-dihydrodibenz[b,e]oxepin-2-acetic acid is about 0.1% (w/v).

* * * * *

UNITED STATES PATENT AND TRADEMARK OFFICE
CERTIFICATE OF CORRECTION

PATENT NO. : 5,641,805
DATED      : June 24, 1997
INVENTOR(S) : Hayakawa et al.

It is certified that error appears in the above-identified patent and that said Letters Patent is hereby corrected as shown below:

On the title page:

under "United States Patent [19]", "Hayakawa et al." should read "Yanni et al."

Item

[75] Inventors:   John Michael Yanni, Burleson;
                  Stella M. Robertson, Arlington, both of Texas;
                  Eiji Hayakawa, Susono;
                  Masashi Nakakura, Shizuoka-ken, both of Japan Signed and Sealed this Eighteenth Day of August, 1998

Attest:

BRUCE LEHMAN

Attesting Officer      Commissioner of Patents and Trademarks

_(12)_ EX PARTE REEXAMINATION CERTIFICATE (10045th)

United States Patent
Yanni et al.

(10) Number: US 5,641,805 C1
(45) Certificate Issued: Feb. 13, 2014

(54) TOPICAL OPHTHALMIC FORMULATIONS FOR TREATING ALLERGIC EYE DISEASES

(75) Inventors: John Michael Yanni, Burleson, TX (US); Stella M. Robertson, Arlington, TX (US); Eiji Hayakawa, Susono (JP); Masashi Nakakura, Shizuoka-ken (JP)

(73) Assignee: Kyowa Hakko Kirin Co. Ltd., Ohtemachi, Chiyoda-Ku, Tokyo (JP)

Reexamination Request:
No. 90/012,720, Nov. 16, 2012

Reexamination Certificate for:
Patent No.: 5,641,805
Issued: Jun. 24, 1997
Appl. No.: 08/469,729
Filed: Jun. 6, 1995

Certificate of Correction issued Aug. 18, 1998

(51) Int. Cl.
*A61K 31/00* (2006.01)
*A61K 31/335* (2006.01)
*A61K 31/45* (2006.01)
*A61P 27/00* (2006.01)
*A61P 27/02* (2006.01)
*A61P 27/14* (2006.01)
*A61K 31/55* (2006.01)
*C07D 313/12* (2006.01)
*C07D 313/00* (2006.01)

(52) U.S. Cl.
CPC ...................................... *A61K 31/00* (2013.01)
USPC .......................................................... 514/450

(58) Field of Classification Search
None
See application file for complete search history.

(56) References Cited

To view the complete listing of prior art documents cited during the proceeding for Reexamination Control Number 90/012,720, please refer to the USPTO's public Patent Application Information Retrieval (PAIR) system under the Display References tab.

*Primary Examiner* — Dwayne Jones

(57) ABSTRACT

Topical ophthalmic formulations of the invention contain as an active ingredient 11-(3-dimethylaminopropylidene)-6,11-dihydrodibenz[b,e]oxepin-2-acetic acid or a pharmaceutically acceptable salt thereof. The formulations are useful for treating allergic eye diseases such as allergic conjunctivitis, vernal conjunctivitis, vernal keratoconjunctivitis, and giant papillary conjunctivitis.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 4 and 8 is confirmed.

Claims 1-3, 5-7 and 9-12 were not reexamined.

* * * * *